(12) United States Patent  
Parker (10) Patent No.: US 7,689,439 B2  
(45) Date of Patent: Mar. 30, 2010

(54) SYSTEM AND METHOD FOR MANAGING MEDICAL DATA

(75) Inventor: Jason Parker, Bromley (GB)

(73) Assignee: Quintiles Transnational Corp., Inc., Durham, NC (US)

( * ) Notice: Subject to any disclaimer, the term of this patent is extended or adjusted under 35 U.S.C. 154(b) by 851 days.

(21) Appl. No.: 11/354,062

(22) Filed: Feb. 14, 2006

(65) Prior Publication Data

US 2007/0191721 A1    Aug. 16, 2007

(51) Int. Cl.
     G06Q 50/00    (2006.01)
(52) U.S. Cl. .................... 705/2; 705/3; 600/300
(58) Field of Classification Search ............. 705/2–3; 600/300  
See application file for complete search history.

(56) References Cited

U.S. PATENT DOCUMENTS

| | | | |
|---|---|---|---|
| 4,388,759 A | 6/1983 | Orejola | |
| 4,601,291 A | 7/1986 | Boute et al. | |
| 4,936,022 A | 6/1990 | Grayzel | |
| 5,305,202 A | 4/1994 | Gallant et al. | |
| 5,319,543 A * | 6/1994 | Wilhelm | 705/3 |
| 5,469,858 A | 11/1995 | Osborne | |
| 5,515,176 A | 5/1996 | Galen et al. | |
| 5,549,654 A | 8/1996 | Powell | |
| 5,605,158 A | 2/1997 | Snell | |
| 5,669,391 A | 9/1997 | Williams | |
| 5,701,894 A | 12/1997 | Cherry et al. | |
| 5,724,985 A | 3/1998 | Snell et al. | |
| 5,792,065 A | 8/1998 | Xue et al. | |
| 5,819,741 A | 10/1998 | Karlsson et al. | |
| 5,891,049 A | 4/1999 | Cyrus et al. | |
| 5,903,889 A | 5/1999 | de la Huerga et al. | |
| 5,911,687 A | 6/1999 | Sato et al. | |
| 6,141,584 A | 10/2000 | Rockwell et al. | |
| 6,325,756 B1 | 12/2001 | Webb et al. | |
| 6,463,320 B1 | 10/2002 | Xue et al. | |
| 6,575,901 B2 | 6/2003 | Stoycos et al. | |
| 6,580,817 B2 | 6/2003 | Badilini | |
| 6,603,464 B1 | 8/2003 | Rabin | |
| 6,640,212 B1 * | 10/2003 | Rosse | 705/9 |
| 6,650,932 B1 | 11/2003 | Menzie et al. | |
| 6,708,057 B2 * | 3/2004 | Morganroth | 600/509 |
| 6,804,656 B1 | 10/2004 | Rosenfeld et al. | |

(Continued)

FOREIGN PATENT DOCUMENTS

WO      98/50873 A      11/1998

(Continued)

OTHER PUBLICATIONS

CORDIGITAL™ Telemedical Solutions, Micro12ECG+ Manual (16 pages), at least as of a 1998.

(Continued)

*Primary Examiner*—Gerald J. O'Connor  
*Assistant Examiner*—Sind Phongsvirajati  
(74) *Attorney, Agent, or Firm*—Kilpatrick Stockton LLP (57) ABSTRACT

According to various embodiments of the present invention, a data management process is provided that manages ECG data collection, review, and reporting in an efficient and secure manner by utilizing biometric checks, quality control measures, and workflow control systems that route data based on a variety of factors to efficiently complete the measurement and analysis process.

24 Claims, 6 Drawing Sheets

U.S. PATENT DOCUMENTS

| | | | |
|---|---|---|---|
| 6,934,578 | B2 | 8/2005 | Ramseth |
| 2002/0059030 | A1 | 5/2002 | Otworth et al. |
| 2002/0172404 | A1 | 11/2002 | Badilini |
| 2003/0060689 | A1* | 3/2003 | Kohls et al. ............... 600/300 |
| 2003/0208378 | A1 | 11/2003 | Thangaraj et al. |
| 2004/0006553 | A1 | 1/2004 | De Vries et al. |
| 2004/0051721 | A1 | 3/2004 | Ramseth |
| 2004/0054296 | A1 | 3/2004 | Ramseth |
| 2004/0204910 | A1 | 10/2004 | Brumbach et al. |
| 2006/0161067 | A1* | 7/2006 | Elion ........................ 600/509 |
| 2006/0167367 | A1* | 7/2006 | Stanczak et al. ............ 600/523 |

FOREIGN PATENT DOCUMENTS

| | | |
|---|---|---|
| WO | WO 00/40145 | 7/2000 |
| WO | WO 02/15818 A2 | 2/2002 |
| WO | WO 03/071391 A2 | 8/2003 |
| WO | WO 2006/086181 A1 | 8/2006 |
| WO | PCT/US07/004150 | 6/2007 |

OTHER PUBLICATIONS

"Magellan ECG Research Workstation Software Operator's Manual," Software Version 2.0, PN 421681-001 Revision C, GE Marquette Medical Systems, Inc., Jan. 10, 2000.

Marquette® HL7 Interface Professional Toolkit Operator's Manual, Software Version 5A PN 40852-30 Revision D (392 pages), Aug. 9, 1999.

Muse CV® Messaging Installation & Configuration—005A & 005B, GE Marquette (16 pages), Jul. 13, 1999.

Muse CV® Web Server Instruction Guide to Enabling SSL, GE Medical Systems Information Technologies, MUSE CV Information System 2003934-001, Revision B (24 pages), Dec. 7, 2001.

Muse CV® Information System Conversions, Forklifts, New Systems, Pre-Quote Survey, Software Version 005C, PN 2002783-029, Revision A, GE Marquette, May 31, 2000.

Physician's Guide to Marquette Electronics Resting ECG Analysis, © Marquette Electronics, Inc., Milwaukee, WI, 1988, 1989, 1990, 1991.

The Card Guard CG-7000DX, 12 Lead ECG Recorder/Transmitter Physician's Guide (22 pages).

TM 2000 Patient Monitoring System, System Requirements Specification, Card Guard Scientific Survival Ltd. Document No. 590043 (46 pages), Jan. 30, 1997.

Bhullar et al., "A Computer Based System for the Study of QT Intervals," Departments of Engineering and Cardiology, University of Leicester, Leicester, UK, IEEE, pp. 533-536, 1992.

Bland, et al., "Statistical Methods for Assessing Agreement Between Two Methods of Clinical Measurement", Department of Clinical Epidemiology and Social Medicine, St. George's Hospital Medical School, London, The Lancet, pp. 307-310, Feb. 8, 1986.

Savelieva, et al., "Agreement and Reproducibility of Automatic Versus Manual Measurement of QT Interval and QT Dispersion," Excerpta Medica, Inc. pp. 471-536,1998.

Lawson et al., "New Method for Digitization and Computerized Analysis of Paper Recordings of Standard 12-Lead Electrocardiograms," IEEE—Computers in Cardiology, pp. 41-44, 1995.

Lepeschkin, M.D. et al., "The Measurement of the Q-T Interval of the Electrocardiogram", From the Division of the Experimental Medicine, University of Vermont College of Medicine and the Bishop De Goesbriand Hospital, Burlington, Vermont Circulation, vol. VI, pp. 378-388, Sep. 1952.

Morganroth, M.D. et al., "How to Obtain and Analyze Electrocardiograms in Clinical Trials: Focus on Issues and Interpreting Changes in the QTc Interval Duration", From the Department of Medicine, University of Pennsylvania, Presented at the University of Pennsylvania Symposium on ECGs in Clinical Drug Development in Philadelphia, Pennsylvania Mar. 30, 1999, pp. 425-433.

Murray et al., "Errors in Manual Measurement of QT Intervals", Br Heart Journal, vol. 71, pp. 386-390, 1994.

Willems et al., "A Reference Data Base for Multilead Electrocardiographic Computer Measurement Programs," J. American College of Cardiology, vol. 10, No. 6, Dec. 1987, pp. 1313-1321.

Willems et al., "Development of a Reference Library for Multi-Lead ECG Measurement Programs," J. Electrocardiology Supplemental Issue Oct. 1987, pp. 56-61.

Willems et al., "Influence of Noise on Wave Boundary Recognition by ECG Measurement Programs," Computers and Biomedical Research, Dec. 20, 1987, pp. 543-562.

Willems, M.D., "CSE Project Leader, Assessment of the Diagnostic Performance of ECG Computer Programs and Cardiologists", Common Standards for Quantitative Electrocardiography, Commission of the European Communities, CSE 10th and Final Progress Report, Dec. 31, 1990, pp. 148-261.

Willems et al., "Common Standards for Quantitative Electrocardiography: The CSE Pilot Study," In: Lecture Notes in Medical Informatics, Lindberg, D.A.B. and Reichertz P.L., eds. New York: Springer Verlag, 11 (1981), pp. 319-326.

MUSE CV® Information System, CPU-CPU/DHCP Interface Installation (Versions of 005A, 005B, & 005C), GE Marquette (16 pages), Mar. 31, 2000.

Department of Health and Human Service's, Food and Drug Administration, Electronic Interchange Standard for Digital ECG and Similar Data; Public Meeting, (4 pages), Published Oct. 24, 2001.

MUSE Version 5C.04 Release Overview, Jan. 14, 2001 (6 pages).

Three (3) Screen Shots of ECGs Produced by G.E. MUSE.

Willems, et al., "The Diagnostic Performance of Computer Programs for the Interpretation of Electrocardiograms," The New England Journal of Medicine vol. 325, No. 25, pp. 1767-1773, Dec. 19, 1991.

The CSE Working Party, "Recommendations for Measurement Standards in Quantitative Electrocardiography," European Heart Journal, (1985) 6, pp. 815-825, 1985, The European Society of Cardiology.

Muse CV ® Information System Operator's Manual, Software Version 005B, PN 421619-001, Revision C, GE Marquette (510 pages), Sep. 8, 1999.

International Business Machines Corporation, "Scheme-Based Work Assignment in a Workflow System", Research Disclosure, Oct. 2000.

Morganroth, et al., "How to Obtain and Analyze Electrocardiograms in Clinical Trials: Focus on Issues in Measuring and Interpreting Changes in the QTc Interval Duration." A.N.E. Oct. 1999, vol. 4, No. 4.

* cited by examiner

SYSTEM AND METHOD FOR MANAGING MEDICAL DATA

FIELD OF INVENTION

This invention relates generally to systems and methods for managing medical data, and more particularly to managing electrocardiogram data in connection with a clinical trial.

BACKGROUND OF THE INVENTION

Various types of patient medical data are valuable pieces of information with respect to a variety of medical practices. These medical practices may include treating, diagnosing, monitoring, and performing clinical trials. Clinical trials are often performed to determine the effect a particular drug may have on a particular type of patient or patients in general. During clinical trials, medical data regarding participating patients needs to be submitted over a period of time. For example, medical data may be required to be submitted before receiving a drug, on a periodic basis while taking a drug, and after the patient has stopped taking the drug.

One type of medical data commonly required during a clinical trial is data from an electrocardiogram (ECG or EKG). To obtain an ECG, medical personnel attach up to 12 leads to various areas on a patient's body. The leads are connected to a device that is able to monitor and record, electronically, the electrical signals measured by the leads with respect to time. The device may be able to display the obtained measurements graphically.

All or part of a patient's medical data may be reviewed by individuals obtaining the data, the person or entity supervising the clinical trial, and a data management company. For instance, during clinical trials involving a drug being administered to a patient, generally an ECG is performed on the patient, and data obtained from the ECG is reviewed, to monitor the patient's health and the effect the drug may have on the patient's heart. ECG data is often sent to other locations besides a testing clinic for review. The ECG data, for example, may be sent to a cardiologist for review and generation of a report based on the data. Clinical trial ECG data generally must be handled confidentially and with great care to ensure the integrity of the clinical trial. Furthermore, the review of the data often must occur relatively quickly, such as within 24 hours, in order to adequately and safely monitor the patient's health.

Conventional processes for reviewing ECG data have involved faxing the ECG data to a data management company. The data management company employs trained technicians that review the data and perform measurements on the ECG data graph to determine information such as a QT, PR, ST, and RR interval. The following, in a non-limiting way, discloses examples of values and how they are determined. The QT interval is measured from the beginning of the QRS complex to the end of the T wave. The QT interval is important for diagnosing prolongation or shortening of the QT interval. A long QT interval signifies an abnormally long delay between the electrical excitation (or depolarization) and relaxation (repolarization) of the ventricles of the heart. A short QT interval involves short QT values that do not significantly change with the heart rate. The QRS value corresponds to the current that causes contraction of the left and right ventricles of the heart. The T wave represents the repolarization of the ventricles.

The PR value is determined as the distance between a P wave and R wave. A P wave is the electrical signature of the current that causes atrial contraction. Its relationship to QRS values determines the presence of a heart block. The R wave indicates contraction of the myocardium, or the muscular tissue of the heart, itself. The ST interval is measured from the QRS complex to the T wave. Like the R wave, the S wave indicates contraction of the myocardium, or the muscular tissue of the heart, itself. The RR value is the interval from the onset of one QRS complex to the onset of the next QRS complex.

A cardiologist is employed to review the ECG and the technician's measurements for accuracy and to create a report. The resulting report is faxed back to the clinical testing center for the patient's records. The report is also faxed to the data management company to collect the information for clinical drug trial reporting purposes.

Recently, computerized systems have been implemented to create, modify, maintain, archive, retrieve, and transmit clinical data. Computerized systems assist data management companies in collecting, handling, and securing clinical trial data. Utilizing a computerized system, ECG data may be transmitted electronically to the data management companies' trained technicians. The technicians are then able to measure the ECG on a computer system screen by using cross hairs associated with a mouse cursor to obtain measurements based on a location of the mouse cursor. Additionally, the technician is able to transmit, electronically, the ECG and measurements from the ECG to a cardiologist for review and generation of a report. The computerized systems allow the technician, cardiologist and the storage facility to be in separate places, including on separate continents, and then allows all concerned to benefit from ideal locations of capacity, data storage, medical expertise, and technical and other desired capacity. Finally, computerized systems provide the ability to electronically transmit ECG data and reports to the clinical trial organizers and to the Federal Drug Administration (FDA) in a format acceptable to the FDA.

Conventional computerized data management systems, however, do not provide sufficient data management processes for securely, efficiently, and safely transmitting and analyzing ECG data. For instance, conventional data management techniques do not provide workflow management functions that promote quick and efficient review of ECG data and reporting. Conventional data management techniques do not provide a high level of security and audit trails to safeguard patient confidentiality and the integrity of the clinical trial. In addition, conventional systems do not provide for automatic quality control procedures to ensure consistency and accuracy with respect to the patient's data. Various embodiments of the present invention, therefore, provide a data management process that includes a high level of patient data security, clinical trial integrity, quality control, workflow management, and ECG review and reporting.

SUMMARY

According to various embodiments of the present invention, data management processes are provided that manage ECG data collection, review, and reporting in an efficient and secure manner. In one embodiment, the present invention provides for receiving ECG data and associated patient data electronically from a clinical test site at a centralized data storage device. The data may be converted to any desirable format for analysis and reporting purposes. The ECG and patient data may then be electronically transmitted to a quality control technician where the technician reviews the data to ensure that patient data matches information previously received involving the particular patient and that the patient data complies with desired or predetermined criteria. Before completing their analysis of the ECG data, the quality control technician may be required to pass a biometric check.

After the quality control technician reviews the data it may then be forwarded electronically to an automated workflow system. In some embodiments, the workflow system is able to forward the ECG data to a technician for measurement. The workflow system may be able to utilize various factors to determine which technician the workflow system should send the ECG data to for measurement. Factors the workflow system may utilize, among others, could include the workload of the one or more technicians for measuring the ECG data, the amount of time left in a particular technician's shift, and the amount of time left before a report on the ECG data is due. Additionally, in some embodiments, the workflow system may remove ECG data electronically from one technician before the technician is able to measure the data and provide it to another technician if the factors utilized by the workflow system indicate that it would be more efficient and quicker. Furthermore, the workflow system may monitor, among other things, the technicians' productivity, efficiency, quality, and accuracy of the ECG measurements based on feedback from a reviewing cardiologist or other source.

A technician may then measure the ECG data and enter the measurements into an electronic table that is associated with the ECG data. Alternatively, a technician may electronically measure the ECG such as by using conventional electronic calipers, and the measurements automatically populate a table electronically. The technician may save the data and be required to provide a biometric signature before the system accepts the technician's measurements. The biometric signature information may be electrically included with the particular ECG data to provide a record of the analysis of the ECG data. The workflow system then sends the ECG data, patient data, and measurements to a cardiologist workflow system, which sends the information to a cardiologist to review. The cardiologist workflow system controls which one of the available cardiologists should receive the data for review based on a variety of factors. These factors may include the same factors the technician workflow system used to determine which technician to send the data. Similarly, the workflow system may remove data from the cardiologist if the cardiologist has not reviewed the data and factors such as time constraints, efficiency, and the criteria of the protocol suggest that sending to another cardiologist would be preferred.

The cardiologist reviews the ECG data and the measurements made by the technician for accuracy. Based on the results of the review the cardiologist may send the ECG data back to the technician for another measurement or create a report to be transmitted to the testing clinic, to the clinical trial supervisors, and, ultimately, to the FDA for review. The cardiologist may be required to provide biometric information before saving or sending a report to ensure the data's security and the clinical trial's integrity.

An advantage of various embodiments of the present invention is to provide automatic tracking of patient visits to a testing center and to remind the centers if the ECG data has not been received by the system by a certain date.

A further advantage of various embodiments of the present invention is to provide a post-analysis diagnosis system to automatically compare ECG measurements with set criteria and notify interested parties if the data falls outside that set criteria.

A further advantage of various embodiments of the present invention is to provide biometric security steps throughout the management system to provide a high level of security and protect the integrity of the data and analysis.

A further advantage of various embodiments of the present invention is to provide an automatic workflow system for efficiently and quickly routing the workflow, among technicians, cardiologists, and others who process the data, based on their performance, efficiency, and effectiveness, and time constraints related to the information and personnel shifts during various steps of the process.

A further advantage of various embodiments of the present invention is to provide a workplace terminal that permits observation, monitoring and control of the workflow of ECG data through the system.

DETAILED DESCRIPTION

Figure 1:
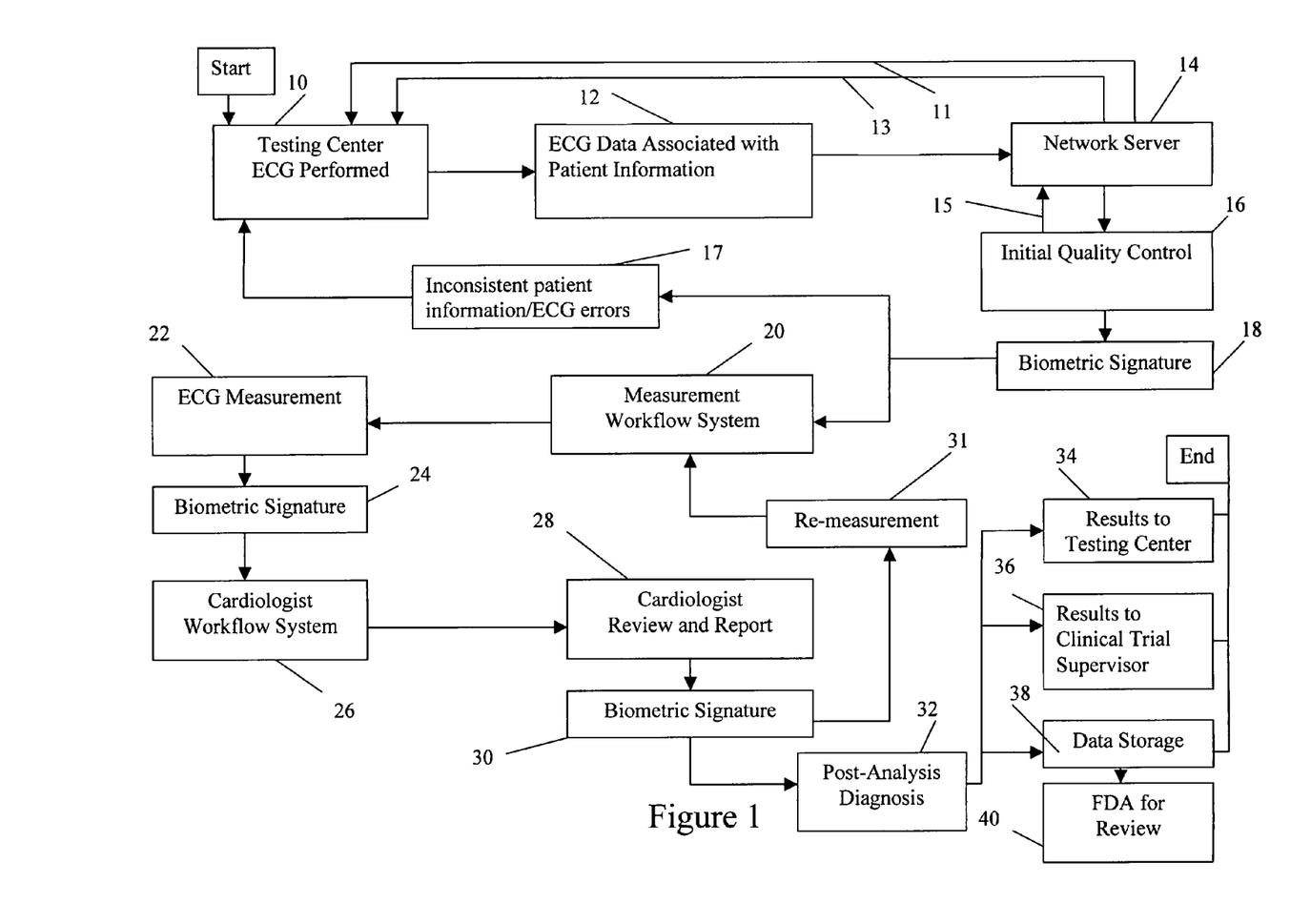
FIG. 1 schematically shows a flow diagram of a data management method according to one embodiment of the invention.

FIG. 1 shows a flow diagram of a data management process and procedure according to one embodiment of the present invention. According to the particular embodiment illustrated in FIG. 1, ECG data is collected 10 from an ECG performed at a clinical testing center. The ECG 10 is preferably administrated by trained medical personnel such as a nurse, doctor, or clinical technician. ECG data is preferably obtained using a plurality of leads attached to various points on the patient's body. An electrical measurement is read from each lead over a period of time and this data is collected and placed in graph format showing voltage or other electrical parameters along with time relative to the starting time. The ECG data is then associated 12 with patient information. Patient information includes demographics such as a patient number associated with the particular patient, date of birth, gender, visit number, date, and time, and testing site number. Patient information is preferably electronically associated 12 with the digital ECG data.

After the patient information is associated with the ECG data 12, the information is transmitted electronically to a server through a network 14. The information is preferably transmitted in digital format. The server 14, which may be located at any location as long as it may be in communication with the network 14, may manipulate the data into a variety of formats for further data management. Preferably, the ECG data is changed into Extensible Markup Language (XML) format. XML format allows the creation of customized tags or metadata that enable the definition, transmission, validation, and interpretation of data between applications and between organizations. In addition, the server preferably transmits a validation signal 11 to the testing center 10 to validate that the information arrived at the server 14.

If a particular patient's ECG data has not reached the server 14 by a certain time, the server preferably transmits a reminder signal 13 to the testing center 10 indicating that a particular patient's ECG data has not been received by the server 14 and that the particular ECG data is overdue. The server 14 may transmit a reminder signal 13 when, for example, the patient has not appeared at the testing center by a scheduled date or an error in the system occurred and the ECG data never reached the server 14.

Next, the server 14 transmits the ECG and patient information electronically to an initial control queue 16. The initial quality control queue 16 may perform a brief overview of the ECG and patient information to check that the data complies with the protocol and/or other desired parameters, e.g. clinical trial criteria and consistency of the patient data compared with previously received patient data. Preferably, either or both a human and a computer system can perform aspects of the overview relative to set criteria and check the data for inconsistencies with previously known patient data. If the human discovers an inconsistency, they may contact the testing center 10 for verification of correct data or to obtain correct data.

Alternatively, a computer system may perform some or all of the initial quality control 16 without human intervention. If a question arises during the initial quality control 16 as to the accurateness of the data or patient qualification, preferably the computer system will automatically issue an electronic communication 17 to the ECG testing center 10 requesting them to verify or correct the information. The ECG testing center 10 will then verify or correct the information and, as before, transmit the ECG data and associated patient information electronically to the server on the network 14. Alternatively, the initial quality control computer 16 may refer errors to a human technician, which it determines according to automated business rules and can quickly be resolved by such human, so that the computer and the human cooperate in resolving problems or issues. Such resolutions, problems or issues may then be forwarded to the testing centers 10. If the initial quality control 16 does not indicate an issue with the data, the ECG data and patient information will be transmitted to the measurement workflow system 20.

In some alternative embodiments of the present invention, when a human performs the initial quality control, the human personnel will be required to provide a biometric signature 18 before transmitting the data to the measurement workflow system 20. A biometric signature 18 may involve, for instance, a device connected to the computer system that is configured to sense one or more unique characteristics of an individual. One example of such a device that is preferably used in the present invention is a reader that is able to read a fingerprint from an individual, identify the individual based on the fingerprint, verify that the individual has permission to perform certain functions, and allow the individual to perform certain functions such as entering data, saving data, and transmitting data. Additionally, information concerning the biometric signature 18, such as the identity of the personnel, time, and date may be electronically associated with the ECG data and patient information. The biometric signature information may be electronically located with the ECG data and patient information and some or all of it may be accessible at any time after its creation. For example, access may be obtained by a third party interested only in quality of the data in a way that also maintains anonymity of the reviewer. Such selective disclosure may also be conducted to comply with the privacy interests associated with any of the organizations or people handling the data or system. Along with the biometric signature 18, the initial quality control reviewer may be required to enter a password before transmitting the data. The password may preferably be correlated with information known about the particular initial quality control reviewer.

After the data has been transmitted to the measurement workflow system 20, the workflow system 20, as explained more fully below, decides which technician to send the ECG data for measurement based on a variety of factors. After receiving the ECG data, in block 22, a measurement technician will measure the ECG data to determine information such as a QT interval and PR interval. The technician preferably measures the ECG data by applying calipers electronically on a computer screen to the ECG graph. The computer preferably automatically populates a table with data from the measurements. Alternatively, the measurement technician may enter data into a table with the data from the measurements. In particular embodiments of the present invention, the measurement technician may be required to provide a biometric signature 24 before performing such tasks as entering, saving, and transmitting data. Similar to the biometric signature above, the biometric signature 24 preferably includes a device, such as a fingerprint reader, connected to the computer system for reading unique features to identify the measurement technician. In addition, the measurement technician may preferably be required to enter a password before saving or transmitting data. The entered password may be correlated with data associated with the particular measurement technician and provide an additional security control measure.

Upon affirmatively identifying the measurement technician and verifying that the particular technician is allowed to have access and the ability to enter, save, or transmit information, the measurement technician is able to transmit the data to a cardiologist workflow system 26. As explained in more detail below, the cardiologist workflow system 26 preferably, based on a variety of factors, decides which cardiologist of the plurality on duty at a particular time should receive the ECG data and measurements for review. The cardiologist may review the ECG data and measurements 28 for measurement accuracy and create a report including whether the ECG data is normal, the technician's measurements are accurate, or the ECG data is abnormal and a recommendation of a plan for follow up with the patient. The report is preferably implemented and supported in data that accompanies or is correlated with the ECG trace information. Furthermore, since the various aspects of the systems preferably communicate electronically, the cardiologist may be located on any continent in which a sufficient number of talented cardiologists are available to provide an efficient and accurate review.

Upon completing the report, the cardiologist may preferably be required to submit a biometric signature 30, which is the same as or similar to the biometric signature disclosed above, before saving the report. The biometric signature 30 preferably includes a device that is capable of reading an individual's fingerprint and correlating that information in a computer system to identify the cardiologist and verify that the particular individual has permission to create, save, and transmit the reports. In addition, the cardiologist may also be required to enter a password. The password may be correlated to data related to the particular cardiologist to provide an additional security measure.

In some embodiments, after the biometric signature 30 has been successfully completed by the cardiologist and the information saved, the ECG data may either be retransmitted to the measurement workflow system 20 for re-measurement by the measurement technician or collected in a completed report 32. If the cardiologist, during the cardiologist review and report 28, indicates in the report that the ECG data should be re-measured by the measurement technician due to various possible reasons, the ECG data will be routed back 31 to the measurement workflow system 20. Alternatively, the ECG data and the cardiologist's report may be routed back 31 to the measurement workflow system 20 and preferably routed to the technician who originally measured the data 22 in order to provide feedback to the technicians for improvement. Possible reasons that the measurement technician may be required to re-measure data include errors made in the original measurement, an inadequate original measurement, and to initiate a quality control measure to ensure accurate measurement and personnel accountability. Alternatively, the measurement workflow system 20 will route the re-transmitted ECG data based on the various factors, discussed in more detail below.

If the ECG data and report is not routed for re-measurement 31, it preferably is transmitted to a computer system for a post-analysis diagnosis 32. The post-analysis diagnosis system 32 is preferably capable of automatically assessing the ECG measurements and cardiologist's report with respect to the criteria of the particular testing protocol associated with the ECG measurements. If the measurements fall outside the criteria set for the testing protocol, the post-analysis diagnosis system 32 preferably automatically notifies the testing center 34 where the ECG was originally performed, the clinical trial supervisor 36, and attaches a note to the particular data and report and sends the information to a data storage 38. Even if the ECG measurements are within the set criteria for the particular protocol, the post-diagnosis system 32 preferably sends the data, patient information, and reports to the testing center 34, clinical trial supervisor 36, and to a data storage system 38. The data storage system 38 preferably collects the data and sends the collected data to the FDA for review 40.

Figure 2:
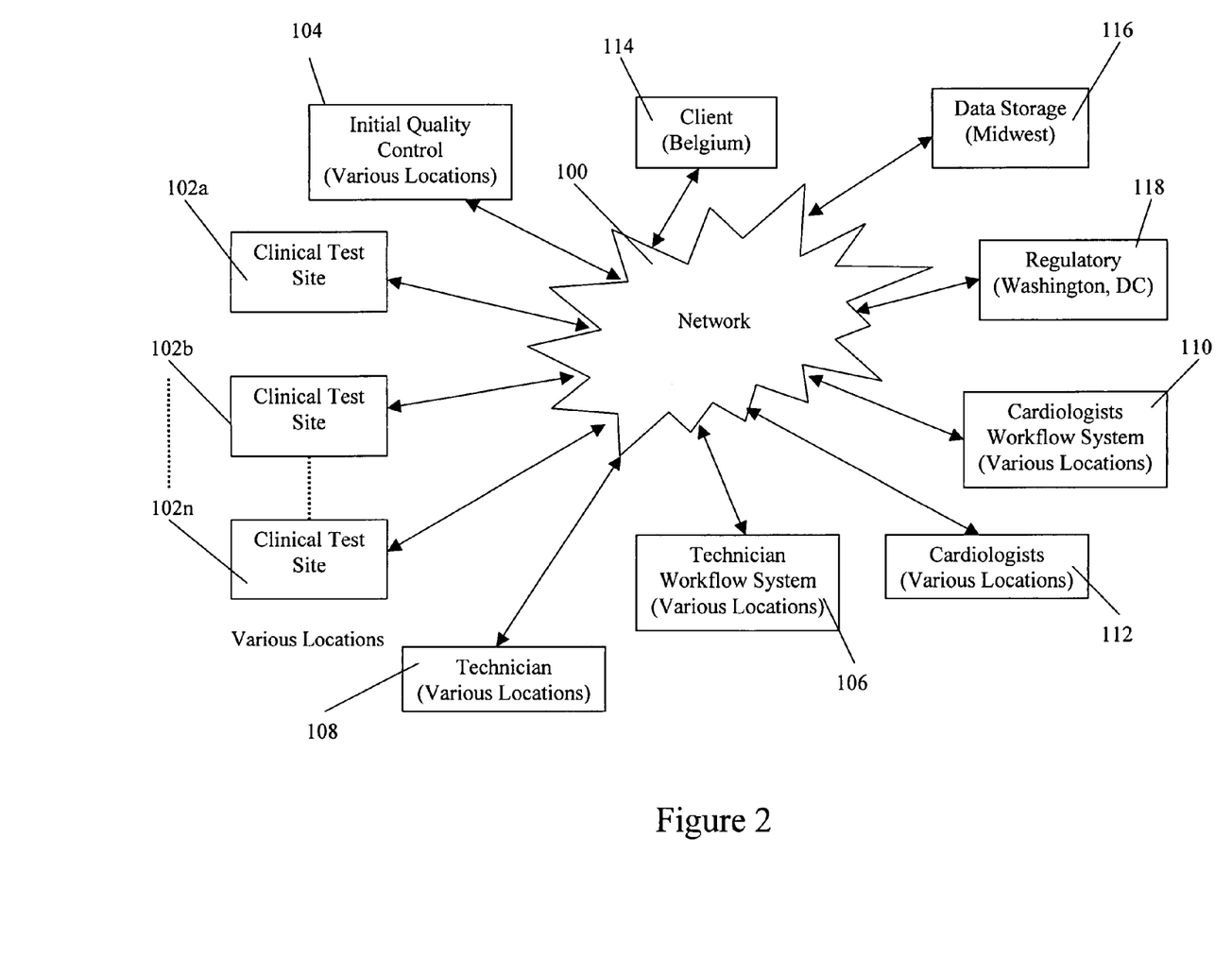
FIG. 2 schematically shows the components of a system which implements the data management method according to one embodiment of the invention.

Referring now to FIG. 2, an example of the data management system and routing to different components in different geographic locations is shown in schematic form. In FIG. 2, the communication and information transfer between the various components of the system may preferably occur through telecommunications and/or data networks 100. The networks 100 may include any system that allows information to be passed from one part of the system to another. Examples of such networks 100 include a computer network, the internet, the public switched telephone network, or a wireless or satellite communications network.

The data management system may include a number of clinical test sites 102a . . . 102n. The clinical test sites 102a . . . 102n preferably perform ECG tests, obtain ECG data, obtain patient information, and transmit the information, along with a destination address, digitally to the network 100. The clinical test sites 102a . . . 102n may be located anywhere in the world and in different locations, as long as it can be connected to a network 100.

The system may send the data and patient information over network 100 to the location designated in the address data. Preferably, the system sends the data and information to an initial quality control 104 located, in the particular embodiment illustrated in FIG. 2 as an example, in the Western United States. The initial quality control 104 may be located at any location, as may the other components of the system. The initial quality control 104 performs a cursory review, either automatically or by human personnel or both, of the data to ensure that all necessary information and data is included in the data file. The initial quality control 104 also preferably confirms with the particular test site 102a . . . n in which the data originated through the network 100 that the data was received. After the initial quality control 104 performs the cursory review, the information and data is sent, through the network 100, to the technician workflow system 106.

Because of the nature of the data management system, the technician workflow system 106 may be located at different locations throughout the world. The technician workflow system 106, after receiving a particular data set will transmit a signal to the initial quality control 104 to provide the initial quality control 104 with confirmation that the information was received. The technician workflow system 106 receives the data and information, including the amount of time left before results from data analysis is due to be completed, and information concerning the technicians 108 currently on duty, such as the amount of time left on their shifts, the volume of ECG data the technician 108 has yet to measure, and the efficiency history of a particular technician 108. The technician workflow system 106 uses the information to determine which technician 108 should receive the data for review in order to quickly and efficiently effectuate the measurements of all received data and the particular data. For instance, a computerized algorithm may be utilized by the technician workflow system to apply different weights to factors and determine which technician 108 should receive the new ECG data for measurement.

Once the technician workflow system 106 determines to which technician 108 to send the data, the technician workflow system 106 will send the data to the technician 108 through the network 100. The technician 108 will measure the ECG data and the measurement results will be included in the electronic data and information file. The technician 108 must also, according to certain embodiments, once ECG measurement is complete or before, provide a biometric signature to ensure the security and integrity of the data. The biometric signature can include electronic information concerning the time, date, personnel identification, or any other information related to the biometric signature. The electronic biometric information is electronically added to the data and information file. After completing the measurements, the technician 108 sends the information to a cardiologist workflow system 110 through the network 100.

The cardiologist workflow system 110 sends the technician 108 an electronic signal when it has received the data so that the technician 108 will have confidence that the data and information was received. As described in more detail below, a cardiologist workflow system 110, according to certain preferred embodiments of the present invention, functions in a manner similar to the technician workflow system 106. For instance, the cardiologist workflow system 110 may be located at any location and utilize a similar algorithm to determine which cardiologist 112 to send the data for review. When the cardiologist workflow system 110 determines to which cardiologist to send the data for review, the cardiologist workflow system 110 will send the data and information to the particular cardiologist 112. The cardiologist 112, who may be located anywhere that provides a pool of competent cardiologists, reviews the data and measurements and creates a report. The report, which preferably is another electronic data element that is attached to the ECG data record, may include, for example, comments concerning the data, recommendations for patient treatment or diagnosis, and directions on where to send the data. Upon completing the report, according to some embodiments, the cardiologist 112 must submit a biometric signature, similar to the technician biometric signature, to ensure the integrity and security of the data and test. Similarly, the biometric signature information will be electronic information that is included in the ECG data record.

Where the ECG data record goes next depends on the cardiologist's 112 report and directions. If the cardiologist 112 indicates a need for re-measurement, the data will be sent to the technician workflow system 106 for distribution to a technician for re-measurement. Preferably, the ECG data will be sent to the technician 108 that originally measured the data in order to provide feedback to the technician and accountability. Alternatively, the ECG data may be distributed to any technician 108 that the technician workflow system determines using the algorithm previously discussed will provide the quickest and most efficient measurement.

If the cardiologist 112 does not indicate a need for re-measurement, the data will be sent, through the network 100, to the clinical test site 102a . . . n that originally performed the ECG test, protocol supervisors 114, a data storage facility that may be located at any location, for example Midwest United States, and ultimately a regulatory agency, such as the FDA in Washington, D.C. The ECG data record may be reviewed, including biometric signature and other history data, by any group or entity with permission to view the record; alternatively, aspects of biometrics or confirmation that the data is protected by biometric signatures but in a manner that protects confidentiality or privacy, can be provided.

Figure 3:
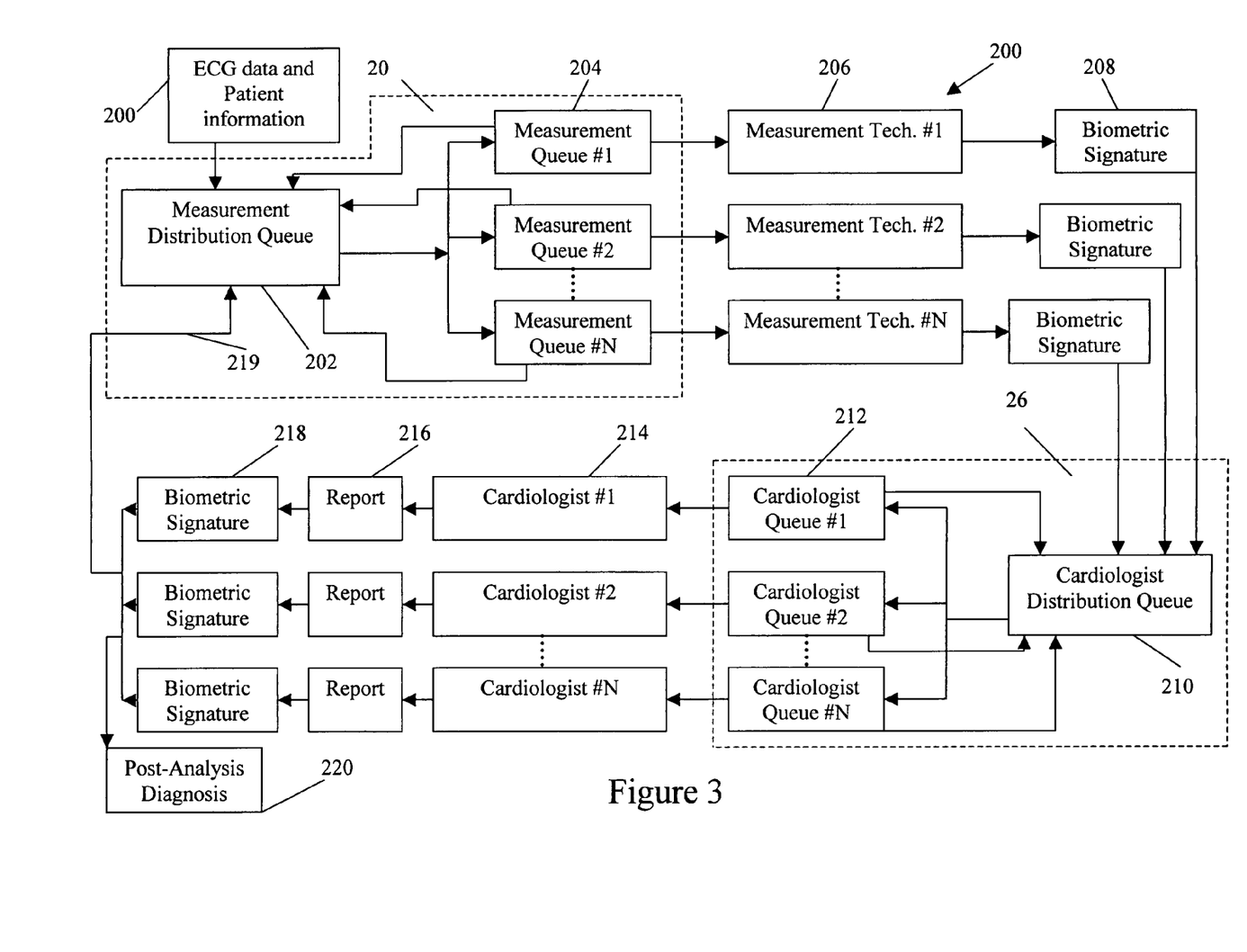
FIG. 3 schematically shows a flow diagram of a workflow related system according to one embodiment of the invention.

Referring now to FIG. 3, illustrated is a more detailed block diagram of the workflow systems 20 and 26 in FIG. 1 according to one embodiment of the present invention. Preferably, the workflow systems 20 and 26 are similar systems and receive and route information based on similar factors. In the particular embodiment illustrated in FIG. 3, ECG data and patient information 200 is in the form of a digital file with several addresses that may be associated with different types of data. The types of data could include, among others, the destination address of the data, the origination address, clinical protocol information, identification of personnel associated with the ECG data, the ECG data, and patient information. The file is transmitted electronically to the measurement workflow system 20 and preferably to the measurement distribution queue 202.

In particularly preferred embodiments, the measurement distribution queue 202 is a processor-based device that includes a processor, storage means, and inputs and outputs. The measurement distribution queue 202 may be in electrical communication with the queues 204 of each measurement technician on duty to send and receive data, commands, and other information. The measurement technician queues 204 are preferably also processor-based devices with a processor, inputs and outputs, and a storage means, and contain information such as the number of ECG data waiting to be measured, identification of each ECG data, the amount of time left on the ECG data before the analysis is to be completed, the abilities and efficiency of particular technicians 106, and the amount of time left on a technician's 206 shift.

Certain preferred embodiments of the present invention utilize the workflow systems 20, 26 and the information related to the ECG data 200 and the on-duty technicians 206 to make the process of reviewing ECG data 100 more efficient, effective and speedy.

According to various embodiments of the present invention, the measurement distribution queue 202 routes received ECG data and patient information 200 to a particular measurement technician 206 based on factors associated with the information from the measurement technician queues 204 and other factors. The processor of the measurement distribution queue 202 determines which measurement technician 206 should receive the ECG data after receiving information concerning the ECG data and the technicians on duty. The processor of the measurement distribution queue 202 then sends the ECG data to the measurement technician queue 204 of the appropriate measurement technician 206 by attaching a destination address in the record associated with the particular ECG data.

Factors which may be utilized by the queue 202 to make decisions about which technicians should be tasked with particular ECG related tasks can include any or all of the following, or any combinations of any of the following: (1) identification of the particular clinical trial, (2) amount of time left before the ECG measurement and analysis needs to be completed, (3) the category or nature of analysis or review that needs to be given to the ECG data, (4) the number of ECGs for a particular clinical trial are already queued for routing to each technician 206, (4) the number of ECGs per category that are already queued for routing to each technician 206, (5) the number of ECGs in general that are queued for routing to each technician 206, (6) the number of technicians 206 on duty at each location, (7) which technicians 206 on duty are qualified to review ECGs for a particular clinical trial or category, (8) the number of technicians 206 on duty generally, (9) the time left on each technician's 206 shift, (10) the cost per unit time for each technician 206 as measured for a particular shift or other desired time interval, (11) any specific circumstances for a trial or ECG that preclude sending the ECG data to particular technicians 206, or technicians 206 in a certain country or location, (12) any specific circumstances for a trial or ECG that preclude or favor sending the ECGs to a particular technician 206 or group of them, (13) the rejection rate of ECGs performed by each technician 206, and/or (14) any other factors as may be desired related to efficiently managing workflow to produce results with adequate quality.

For example, if the technician queue 204 of measurement technician #1 206 contains a relatively high number of different ECG data specimens waiting to be measured by the technician and measurement technician #2's 206 queue 204 contains a relatively low number of different ECG data specimens waiting to be measured, the measurement distribution queue 202 may transmit new ECG data to measurement technician #2's 206 queue 204 for measurement. Additionally, the measurement distribution queue 202 may also remove ECG data from the queue 204 of measurement technician # 1 206 and transmit it to measurement technician #2's 206 queue 204. In determining which measurement technician queue 204 to send new data or remove ECG data from one queue and send it to another queue 204, the measurement distribution queue 202 may also identify, for example, the ECG data in the respective technician queues 204 and determine the amount of time left on each ECG data before the analysis is scheduled to be complete. Furthermore, the measurement distribution queue 202 may obtain information associated with the respective measurement technicians 206. More specifically, for example, the measurement distribution queue 202 may obtain the amount of time left on the measurement technician's 206 shift, and use the information to determine the number of ECG data that should be in the respective queues for measurement.

As described above, after the measurement technicians 206 perform their measurements, in some embodiments of the present invention, the measurement technicians 206 may be required to provide a biometric signature 208. As stated previously, the biometric signature 208 preferably includes a device that is able to read the fingerprint from the measurement technician 206. The device then, for example, compares the fingerprint with a database containing the fingerprints of the plurality of measurement technicians, an identification associated with the fingerprint, and information concerning what the measurement technician 206 may electronically save or transmit. Once the measurement technician 206 has successfully provided a biometric signature 208, information such as the time, date, and identification of the particular measurement technician 206 may preferably be electronically attached to the particular ECG data. Attaching the biometric signature 208 may, for example, provide an audit trail to provide interested and allowed parties to recreate the path with which particular ECG data passed while in an analysis and reporting system. Selectively disclosing data provides data verification quality control while protecting any privacy interests associated with the data or the collection, management, and analysis personnel.

After the measurement technician 206 successfully provides a biometric signature 208, the ECG data, associated measurements, and patient information may be transmitted electronically to a cardiologist distribution queue 210. The cardiologist distribution queue 210 may preferably function similar to the measurement distribution queue 202. For instance, the cardiologist distribution queue 210 may be in electrical communication with a plurality of cardiologist queues 212, which are each associated, respectively, with an on-duty cardiologist 214. In certain embodiments of the present invention, the cardiologist distribution queue 210 is able to utilize information regarding the ECG data and on-duty cardiologists to determine which cardiologist queue 212 to send new ECG data and measurements for review or whether to remove ECG data and measurements from a particular cardiologist's queue 212 and send the ECG data and measurements to another cardiologist's queue 212.

Factors which may be utilized by the queue 210 to make decisions about which cardiologists should be tasked with particular ECG related tasks can include any or all of the following, or any combinations of any of the following: (1) identification of the particular clinical trial, (2) amount of time left before the ECG measurement and analysis needs to be completed, (3) the category or nature of analysis or review that needs to be given to the ECG data, (4) the number of ECGs for a particular clinical trial are already queued for routing to each cardiologist 214, (4) the number of ECGs per category that are already queued for routing to each cardiologist 214, (5) the number of ECGs in general that are queued for routing to each cardiologist 214, (6) the number of cardiologists 214 on duty at each location, (7) which cardiologists 214 on duty are qualified to review ECGs for a particular clinical trial or category, (8) the number of cardiologists 214 on duty generally, (9) the time left on each cardiologist's 214 shift, (10) the cost per unit time for each cardiologist 214 as measured for a particular shift or other desired time interval, (11) any specific circumstances for a trial or ECG that preclude sending the ECG data to particular cardiologist 214, or cardiologists 214 in a certain country or location, (12) any specific circumstances for a trial or ECG that preclude or favor sending the ECGs to a particular cardiologist 214 or group of them, (13) the rejection rate of ECGs performed by each cardiologist 214, and/or (14) any other factors as may be desired related to efficiently managing workflow to produce results with adequate quality.

For example, the cardiologist queue 212 for cardiologist #1 214 has a relatively high number of ECG data or if there is a relatively low amount of time left in cardiologist # 1's 214 shift, the cardiologist workflow system 210 may send additional ECG data and measurements to another cardiologist queue 212. In addition, the cardiologist workflow system 210 may also remove data from the queue for cardiologist #1 214 and send it to another cardiologist queue 212, such as, for example, the queue 212 for cardiologist #2 214.

After a cardiologist 214 reviews the ECG data and measurements, the cardiologist preferably generates a report 216 indicating the cardiologist's analysis, recommendation, or direction for the measurement technician to re-measure the ECG data. The report 216 may form a part of the data that accompanies or is correlated to the ECG data being reviewed. Before saving and sending the data, however, the cardiologist 214 may preferably be required to provide a biometric signature 218. The cardiologist biometric signature 218 is preferably similar to the technician biometric signature 208. For instance, the biometric signature 218 may preferably include a device that is able to read fingerprints and a computer system that is electronically connected to the device. The computer system may correlate the fingerprint reading and identify the particular cardiologist, verify that the particular cardiologist has permission to perform the saving or transmitting function, or any other desired function, and allow the verified cardiologist to perform the function. The biometric signature data may preferably form a part of or be correlated to the particular ECG data to allow interested persons to later, for example, identify the particular cardiologist that created the report and the time the report was created.

If the reviewing cardiologist 214 indicates the need for a re-measurement of the ECG data, the ECG data, report, and other information may be redirected 219 to the technician distribution queue 202 for re-measurement by the technician 206. Preferably, the same technician 206 that performed the original measurement may receive the redirected ECG data. After the ECG data is re-measured by technician 206 and a biometric signature 208 is successfully applied, the data re-enters the cardiologist queue 210 for a cardiologist 214 to review.

If the reviewing cardiologist 214 does not indicate a need for re-measurement, the ECG data may preferably be transmitted to post-analysis diagnosis system 220 that will compare the ECG measurements and other data to criteria set by the particular testing protocol in order to provide an additional quality control measure and the patient with an additional safety control measure. If the ECG data falls outside the set criteria, the post-analysis diagnosis system 220 preferably automatically transmits a notice to the original ECG testing center, the clinical trial supervisor, and to the particular ECG data to be sent to a data storage system. Furthermore, the post-analysis diagnosis system 220 may provide feedback to the cardiologists 214 and the cardiologist workflow system 26, if the cardiologist 214 did not note that the data was outside the protocol criteria. If the ECG measurements are within set criteria, the post-analysis diagnosis system 220 preferably transmits the ECG data and measurements, patient information, and cardiologist report to the ECG testing center, clinical trial supervisor and data storage system.

Figure 4:
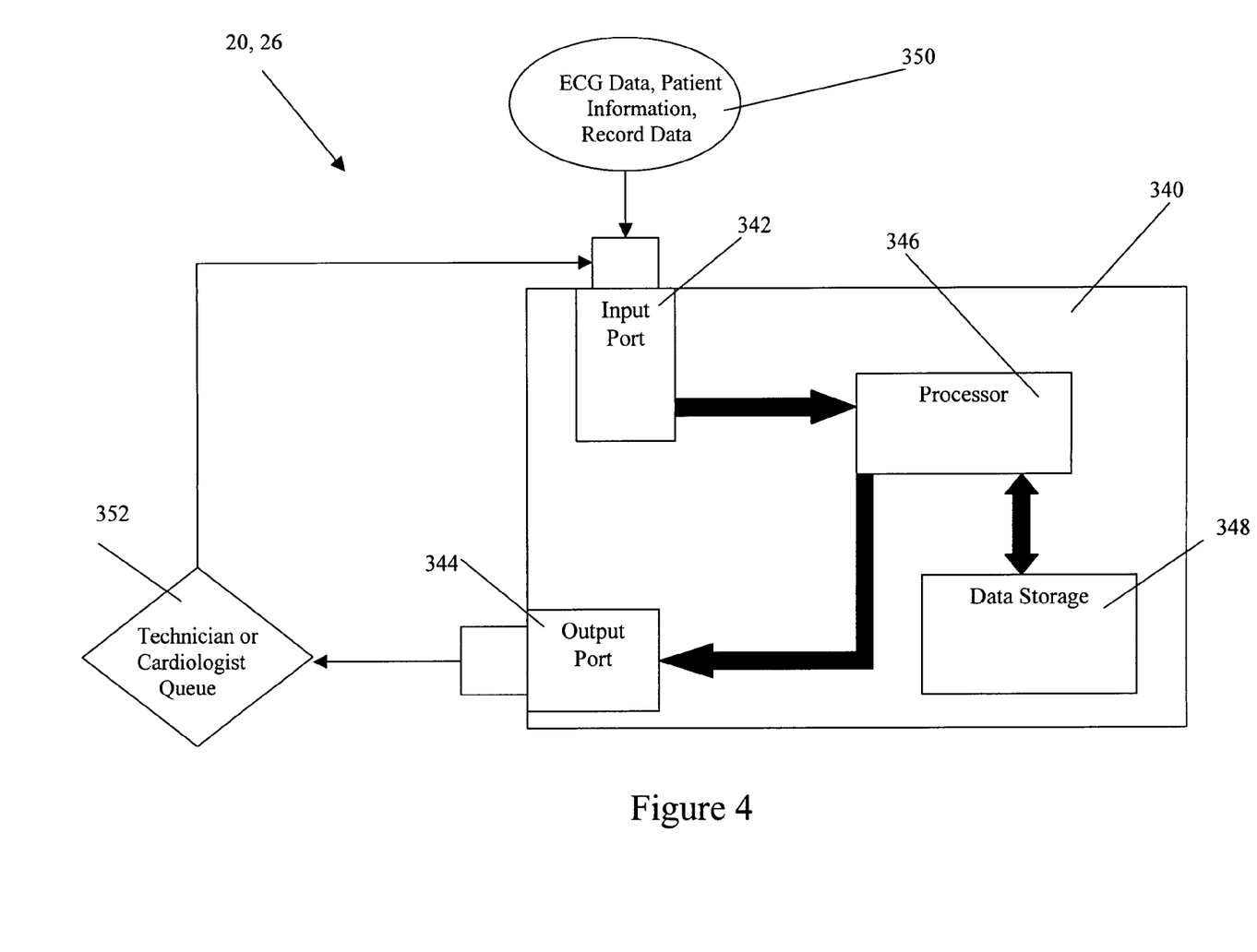
FIG. 4 schematically shows a flow diagram of a platform which may be used to carry out aspects and processes according to one embodiment of the invention.

Referring now to FIG. 4, illustrated is another embodiment of the workflow systems 20, 26. Both the measurement technician workflow system 20 and cardiologist workflow system 26 may preferably include a processor-based device 340, such as a computer system, with input 342 and output 344 ports, a processor 346 and data storage 348. The processor 346 may receive input data 350 from ECG data, patient information, record data, or any other information related to the ECG system through one or more inputs 342. In addition, the processor 346 may receive, through input port 342, information related to particular technicians or cardiologists from the technician or cardiologist queues 352. The received data may be stored in a data storage device 348, such as a hard drive or random access memory. The processor 346 preferably utilizes the data and transmits stored information or commands to the technician or cardiologist queues 352 through one or more outputs 344.

Figure 5:
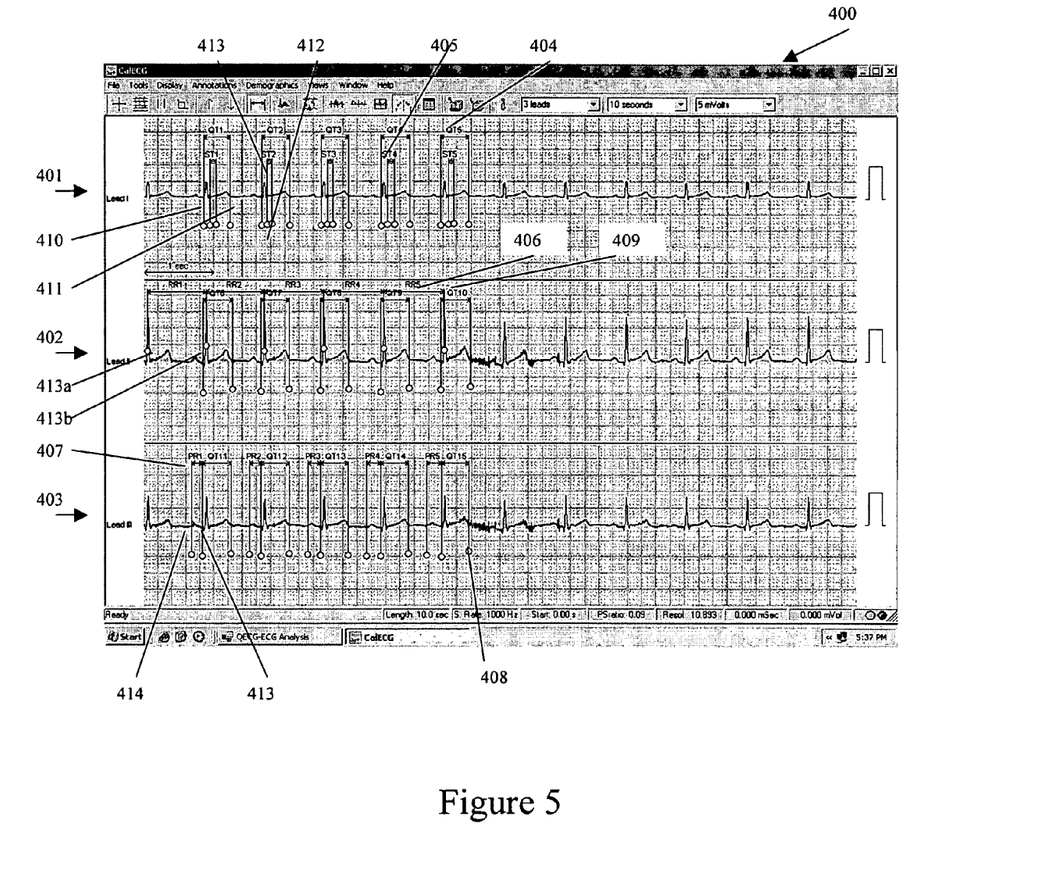
FIG. 5 schematically shows an example of graphed ECG data and measurements according to one embodiment of the invention.

Referring now to FIG. 5, illustrated is sample ECG data that is graphed with measurements according to one embodiment of the present invention. In FIG. 5, the ECG data 400 includes data from three leads 401, 402, 403 and is shown as a function of voltage with respect time. Although the specific traces shown in FIG. 5 only illustrate data from three leads 401, 402, 403, alternative embodiments of the present invention provide for ECG data from any number of leads to be shown, which can be done in a conventional manner.

According to the specific embodiment illustrated in FIG. 5, measurements for the QT 404, ST 405, RR 406 and PR 407 values are shown. A measurement technician has already applied electronic calipers 408 to the ECG data 400 with labels 409 indicating the particular measurement type. As illustrated, the QT 404 value is preferably measured on all three lead ECG data 400 and is measured from the start of the Q wave 410 to the end of the T wave 411. Alternatively, the QT value may be obtained from one of the leads 401, 402, 403. The ST value 405 is preferably measured from at least one lead with ECG data 400 and is the distance between the QRS complex wave 413 and the T wave 412. The RR value 406 is preferably measured from the beginning of one QRS complex wave 413a to the beginning of the next QRS complex wave 413b. The RR value 406 is preferably measured from ECG data 400 from at least one lead. The PR value 407 is preferably measured from ECG data 400 from at least one lead and is measured from the P wave 414 to the QRS complex wave 413.

Each of the above measurements is preferably performed a plurality of times on one or more lead samples of ECG data 400. After accumulating the measurements for each value, a data table is preferably automatically populated with the values such as average values for each type of measurement. Alternatively, the data table is automatically populated with a value for each measurement for each data type or automatically populated with any other data based on the cumulative data. In still other embodiments of the present invention, the measurement technician may manually enter the data associated with the ECG data measurements into tables. The tables are then electronically associated with the ECG data and are accessible for future review by a reviewing cardiologist, clinical trial supervisor, testing center personnel, the FDA, or any other entity with permission to view the measurements.

In some embodiments of the present invention, a terminal is provided that is in electrical communication with, for example, the servers, initial quality control, measurement workflow system, cardiologist workflow system, and the post-analysis diagnosis system. The terminal preferably provides the ability to track where each ECG data file is located in the system at any particular time and to determine the status of such ECG data, as well as allowing other observation, monitoring and control over flow of data and work in the system.

Figure 6:
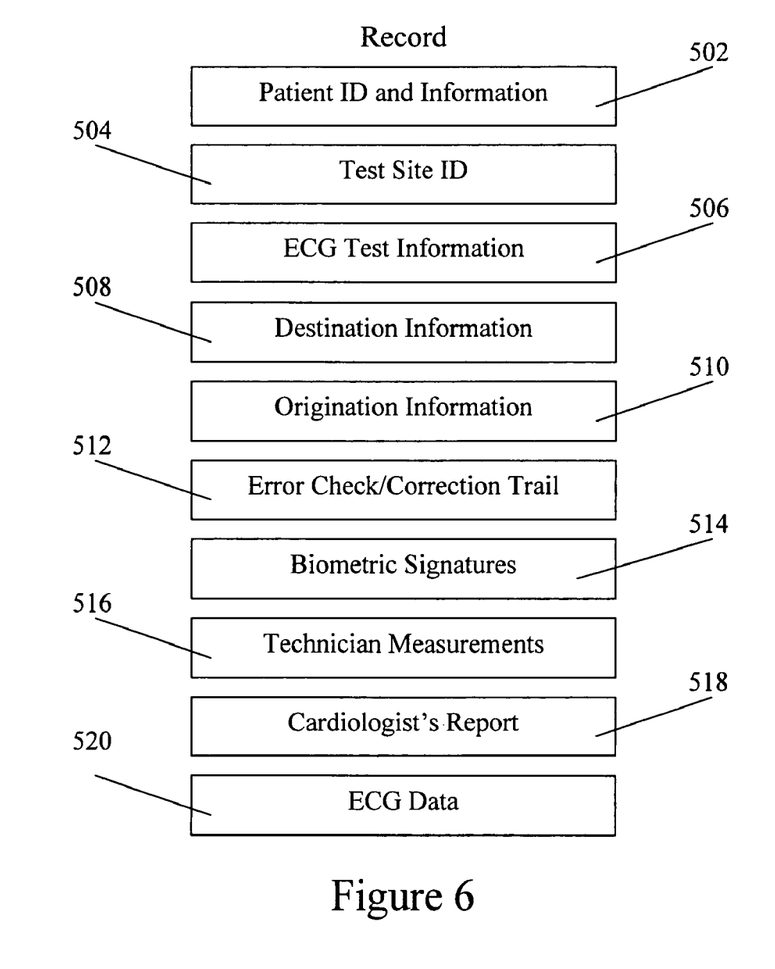
FIG. 6 shows a schematic of a data record that may accompany the data of FIG. 5.

Referring now to FIG. 6, illustrated are data elements of an ECG record according to one embodiment of the present invention. Data records preferably include information related to the ECG data and may contain the ECG data themselves and are preferably an electronic file that is transferred between the different elements of the data management system of the present invention. The particular data record shown in FIG. 6 includes a number of different types of data 502-520. For example, the record may include patient identification and information 502 such as a name or number that may be associated with a name, gender, age, race, or any other patient information pertinent to a clinical trial. Another data record may include test site identification 504 information, such as the testing center location, personnel identification, or any other information related to the test site.

The record may also include test protocol information 506, such as the test protocol, drug or medical procedure being tested, or special information related to the test protocol. The test protocol information 506 may also include normal or acceptable data parameters, such as normal ECG measurement ranges or any other type of information related to the test protocol.

The record may also include destination 508 and origination 510 information. Destination 508 and origination 510 information may include, for example, the location, time, and date of the data management component that is the origination or destination of ECG information and the record at each transfer instance in the system.

In addition, the record may include error check/correction trail information 512 to provide a digital check on the ECG data and insure the integrity and accuracy of the digital ECG data. Furthermore, biometric signature data 514, such as the time and date of the biometric signature and identification of a particular technician or cardiologist that performed measurements or analyzed the data, may be included in the record.

Technician measurement data 516 and the cardiologist's report 518 may also be included in the record after each of the technician measurement and cardiologist's report, respectively, has been completed. The technician measurement data 516 may include the results from the technician's measurements of the ECG data. The cardiologist's report 518 may include the results from the cardiologist's review of the data, including any comments regarding the ECG data, recommendations as to diagnosis or treatment, and recommendations on whether the patient should continue participating in the protocol. Finally, the record includes the digital ECG data 520. The ECG data 520 includes digital version of the values of the electrical signals with respect to time, as obtained at the test site.

The following describes a specific predictive example of data management according to a specific preferred embodiment of the present invention. A clinical trial is first planned and a protocol developed. The protocol typically includes the testing site information, visit schedule information, and the ECG criteria. The data management company enters the criteria electronically into their workflow systems, quality check systems, and post-analysis diagnosis systems to compare to the ECG data, measurements, and analysis.

Patients agreeing to participate in the clinical trial visit testing centers to receive medication according to the trial, submit to an examination, and otherwise provide information based on the examinations and testing such as ECG data. Personal information is entered into a database located at the testing center. An identification number is associated with the patient's name and replaces the name to ensure patient privacy. Information from testing, such as ECG data, is converted to a digital format, and associated with the patient's information by creating an electronic record with several fields and entering the digital ECG data and patient information into the fields.

The record containing ECG data and patient information is then transmitted through a conventional telecommunications or data network to a network server. The network server uses E-Scribe provided by Mortara located in Milwaukee, Wis. or GE Marquette MUSE receiving software and hardware provided by GE Medical Systems located in Milwaukee, Wis. to convert the ECG data to the XML format. The network server also sends a full hand shaking data packet back to the transmitting ECG device to inform the testing center that the data was received. The network server then forwards data to an initial quality control. Upon receipt, the initial quality control informs the network server indicating that the data was received.

The initial quality control includes a computer system connected to the network that receives the data and displays the patient information and ECG data on a screen for an initial quality control technician to review the data for inconsistencies. If previous patient information is present on a database accessible by the initial quality control computer, that information can displayed side-by-side with the new patient information on the computer screen. The initial quality control reviews the sets of information for inconsistencies and for incorrect information, such as a patient age of 130 years. If the initial quality control review indicates inconsistent or incorrect data, a data correction form is transmitted to the original testing center seeking verification or correction of the data. If no inconsistent or incorrect data are detected, or if the data is verified or corrected by the original testing center, the initial quality control sends the data record electronically to a measurement workflow system. Such error correction and/or messaging can also be conducted automatically using rules or partially automatically with the aid of a reviewer.

Before the information is electronically transmitted to the measurement workflow system, the initial quality control can require a biometric signature. The biometric signature is performed through the U-Match Matchbook version 3.0 hardware, utilizing Athenteon Software Appliances version 1.0 (BSDK 4.7 and 5.0), all provided by BioLink Technologies International, Inc. located in Coral Springs, Fla., which is connected to a database that contains biometric information associated with the technicians. If the technician submitting the biometric data is authenticated, validated, or permissioned by information in the database, the technician may be authorized to transmit the record. Once the biometric signature is determined to be valid, the identification of the personnel, time, and data of the signature is automatically electronically entered into the record with the ECG data. If the technician is not identified, the biometric signature system would not allow the technician to transmit the data.

The measurement workflow system receives the electronic data record of the ECG data, along with electronic data associated with the measurement technicians on duty. Such data associated with the technicians includes the number of technicians on duty, the time for each technician remaining on shift, the number of ECG data records waiting to be measured by each technician. The workflow system manages the volume of ECG data to be measured by allocating the data to the technician who is in best position to process it according to these criteria and this determination.

Once the workflow system determines to which technician to send the ECG data for measurements, the workflow system sends the particular record to that technician's queue. The technician queue stores the information while waiting for the technician to measure the ECG data already waiting in the technician queue. The technician queue can also notify the technician when the allocated time for a particular ECG data record to be measured is near expiration. The technician queue notifies the technician by listing each ECG data set waiting to be measured and highlighting the records in red with only an hour left on the allocated time, in yellow with between 1 and 2 hours left, and in green with more than 2 hours left. The technician is able to view the technician queue screen and select the particular ECG data with the least amount of time left in the technician's particular queue.

After selecting the particular ECG data, the technician utilizes CalECG version 2.0 software provided by A.M.P.S. located in Montichiari, Italy to obtain the ECG data in the form of a graph of the voltage with respect to time of three leads. The technician then uses the CalECG electronic caliper software provided by A.M.P.S. located in Montichiari, Italy to measure the desired values of QT, ST, RR, and PR on the graphed ECG data on a computer screen by locating the calipers with a mouse on the appropriate points on the graphed ECG data. When these values are measured, the value associated with these measurements automatically populates an electronic table and is entered into the ECG data record upon the technician saving the measurements. Similar to the initial quality control, before the technician saves the data, the technician must submit a biometric signature by using the U-Match Matchbook version 3.0 hardware, utilizing the Athenteon Software Appliances version 1.0 (BSDK 4.7 and 5.0), provided by BioLink Technologies International, Inc. located in Coral Springs, Fla. If the technician has permission to save, the measurement data will be included into a field of the ECG record and electronic sent to a cardiologist workflow system.

The cardiologist workflow system is able to receive the information related to the amount of time left before the ECG data measurement and analysis must be completed, along with electronic information related to the particular cardiologists on duty. Such information includes the number of cardiologists on duty, the number of ECG data records waiting to be analyzed by each cardiologist, the cost per unit of time for each cardiologist, the cardiologist's historical efficiency and accuracy, and other relevant information including amount of time left before the ECG data analysis is due to be completed. The cardiologist workflow system will, based on the information related to the ECG data and cardiologists, send the ECG data for review to the cardiologist that will most efficiently complete the analysis of the data. For instance, if the time left for the ECG data to be completed is 6 hours, the workflow system will determine which cardiologist would be most efficient at measuring the data while calculating, also, the possibility that ECG data that is later received by the workflow system may have only an hour left before it is to be completed.

Once the workflow system determines which cardiologist should receive the ECG data for analysis, the workflow system will electronically assign the ECG data to the particular cardiologist's queue. The cardiologist queue stores the ECG data and displays the presence and status of the data to the cardiologist while the cardiologist is measuring other ECG data. The technician queue will highlight the ECG data waiting to be analyzed in red if the time left until completion of that particular ECG data is less than 1 hour. If the time left is between 1 and 2 hours, the ECG data will be highlighted in yellow, while ECG data with time left of more than 2 hours will be highlighted in green.

The cardiologist uses the system to access the ECG data by clicking on the particular data to be measured. The system accesses the ECG data, patient information, and technician measurement data and displays the information on a screen viewable by the cardiologist. The cardiologist reviews the data and provides comments regarding whether the ECG data is (1) correctly measured by the technician, (2) if correctly measured, whether the ECG data is normal, (3) if abnormal, the recommended treatment, diagnosis or changes within the protocol should be made. The cardiologist also performs other analysis and supplies information and conclusions in a report, which may form part of the data.

Once the cardiologist completes the report, they will save the data after providing a biometric signature that is the same as or similar to the one previously described. The biometric signature data, when completed and successful, along with the cardiologist's report, will be entered into fields of the particular ECG data record and saved. If the measurements are incorrect, the cardiologist sends the data electronically to the measurement workflow system for re-measurement. The measurement workflow system will electronically read the audit trail associated with the ECG data and send the ECG data for re-measurement to the same technician who originally measured the data to provide feedback to the measurement technicians. If the measurements are correct, however, the report is transmitted electronically to a post-diagnosis analysis system.

The post-diagnosis analysis system is a computer system that can access a database with set protocol criteria relating to ECGs. The post-diagnosis analysis system receives the ECG data record and electronically compares the measured ECG values with the protocol ECG criteria to make sure that the ECG values are within the ECG criteria and thus provides an additional quality and safety check on the clinical test. If the ECG values are outside the set criteria, the post-analysis diagnosis system will deliver a message indicating values outside the set range to the original testing center and clinical trial supervisors.

Ultimately, after the data have been prepared and verified by the system, one or more reports is generated regarding the ECG information and accompanying trial information for transmission electronically and as otherwise desired to the original testing center, clinical trial supervisors, data storage facility, and ultimately to the FDA.

What is claimed is:

1. A system comprising:
   a technician workflow system comprising a processor capable of causing the technician workflow system to:
      receive electrocardiogram (ECG) data associated with a requested review completion time, the ECG data being associated with at least one patient participating in a clinical trial, the requested review completion time being associated with the clinical trial;
      receive a number representing an amount of distributed ECG data present in each technician queue associated with at least one technician among a plurality of technicians,
      determine a technician among the plurality of technicians to receive the ECG data that is associated with the requested review completion time based on the requested review completion time and the amount of distributed ECG data present in each technician queue to allow the technician among the plurality of technicians to obtain a measurement of the ECG data before the requested review completion time; and
      provide the ECG data associated with the requested review completion time to a technician queue of the technician among the plurality of technicians determined to receive the ECG data; and
   a cardiologist workflow system comprising a system processor capable of causing the cardiologist workflow system to:
      receive the ECG data and the measurement from the technician workflow system;
      receive a number representing an amount of distributed ECG data present in each cardiologist queue that is associated with at least one cardiologist among a plurality of cardiologists,
      determine a cardiologist among the plurality of cardiologists to receive the ECG data and the measurement based on the requested review completion time and the amount of distributed ECG data present in each cardiologist queue to allow the cardiologist among the plurality of cardiologists to review the measurement made by the technician of the ECG data before the requested review completion time;
      provide the ECG data associated with the requested review completion time to a cardiologist queue of the cardiologist among the plurality of cardiologists determined to receive the ECG data; and
      receive a report created by the cardiologist among the plurality of cardiologists, the report comprising a result of the review by the cardiologist of the measurement.

2. The system of claim 1, further comprising:
   an initial quality control system configured to:
      receive the ECG data associated with the requested review completion time and patient information of a plurality of patients associated with the ECG data from at least one testing center;
      analyze the ECG data for one or more errors by comparing the ECG data to pre-set ECG parameters; and
      analyze the patient information for one or more errors by comparing the patient information to patient information parameters,
   wherein the technician workflow system is configured to receive the ECG data and the patient information from the initial quality control system.

3. The system of claim 1, further comprising:
   a post-analysis diagnosis system configured to:
      receive the report;
      compare the measurement in the report to a predetermined parameter range;
      transmit a notification to the cardiologist workflow system if the measurement is outside the predetermined parameter range, the notification comprising the measurement, the ECG data, and an identification of measurement as being outside the predetermined parameter range; and
      transmit the report to at least one testing center if the measurement is within the predetermined parameter range.

4. The system of claim 3, wherein the post-analysis diagnosis system is configured to:
   receive a confirmation from the cardiologist workflow system in response to the notification that the measurement is outside the predetermined parameter; and
   transmit the report to the at least one testing center.

5. The system of claim 1, wherein the technician workflow system is configured to:
   receive a biometric signature from the technician, the biometric signature identifying the technician;
   associate the biometric signature with the ECG data; and
   transmit the ECG data to the cardiologist workflow system only if the biometric signature is valid.

6. The system of claim 1, wherein the cardiologist workflow system is configured to:
   receive a biometric signature from the cardiologist, the biometric signature identifying the cardiologist;
   associate the biometric signature with the ECG data; and
   receive the report from the cardiologist only if the biometric signature is valid.

7. The system of claim 1, wherein the cardiologist workflow system is configured to determine the cardiologist among the plurality of cardiologists to receive the ECG data and the measurement based on the requested review completion time and the amount of distributed ECG data present in each cardiologist queue by:
  determining a shift ending time for each cardiologist of the plurality of cardiologists; and
  identifying the cardiologist of the plurality of cardiologists having an ability to review the ECG data and the measurement before the requested review completion time and before the shift ending time for the cardiologist.

8. The system of claim 1, further comprising:
a server device capable of determining an absence of ECG data for a patient at an end of an expected receipt time and transmitting a notification to the at least one testing center, the notification indicating that the ECG data for the patient is overdue.

9. The system of claim 1, wherein the cardiologist workflow system is configured to:
  receive the report comprising a command to re-measure the ECG data; and
  transmit the ECG data to the technician workflow system for re-measurement by a technician among the plurality of technicians in response to the command.

10. A method comprising:
  receiving electrocardiogram (ECG) data associated with a requested review completion time, the ECG data being associated with at least one patient participating in a clinical trial, the requested review completion time being associated with the clinical trial;
  determining, by a technician workflow system, a technician among a plurality of technicians to receive the ECG data associated with the requested review completion time based on the requested review completion time and an amount of distributed ECG data present in each technician queue of a plurality of technician queues to allow the technician among the plurality of technicians to obtain a measurement of the ECG data before the requested review completion time, the technician workflow system comprising a processor capable of causing the technician workflow system to determine the technician among the plurality of technicians to receive the ECG data;
  providing, by the technician workflow system, the ECG data associated with the requested review completion time to a technician queue associated with the technician among the plurality of technicians determined to receive the ECG data; and
  receiving the ECG data and the measurement from the technician workflow system;
  determining, by a cardiologist workflow system, a cardiologist among a plurality of cardiologists to receive the ECG data and the measurement by the technician based on the requested review completion time and an amount of distributed ECG data and distributed measurements present in each cardiologist queue of a plurality of cardiologist queues to allow the cardiologist among the plurality of cardiologists to review the measurement made by the technician of the ECG data before the requested review completion time, the cardiologist workflow system comprising a processor capable of causing the cardiologist workflow to determine the cardiologist among the plurality of cardiologists to receive the ECG data and the measurement by the technician;
  providing, by the cardiologist workflow system, the ECG data associated with the requested review completion time to a cardiologist queue associated with the cardiologist among the plurality of cardiologists determined to receive the ECG data; and
  receiving a report created by the cardiologist among the plurality of cardiologists, the report comprising a result of the review by the cardiologist of the measurement.

11. The method of claim 10, further comprising:
  receiving the ECG data associated with the requested review completion time and patient information of at least one patient associated with the ECG data from a testing center;
  analyzing the ECG data for one or more errors by comparing the ECG data to pre-set ECG parameters;
  analyzing the patient information for one or more errors by comparing the patient information to patient information parameters; and
  sending a notification to the testing center if the one or more errors for the ECG data or for the patient information is detected.

12. The method of claim 10, further comprising:
  comparing the measurement in the report to a predetermined parameter range;
  transmitting a notification to the cardiologist workflow system if the measurement is outside the predetermined parameter range, the notification comprising the measurement, the ECG data, and an identification of measurement as being outside the predetermined parameter range; and
  transmitting the report to at least one testing center if the measurement is within the predetermined parameter range.

13. The method of claim 12, further comprising:
  receiving a confirmation from the cardiologist workflow system in response to the notification that the measurement is outside the predetermined parameter; and
  transmitting the report to the at least one testing center.

14. The method of claim 10, further comprising:
  receiving a biometric signature from the technician, the biometric signature identifying the technician;
  associating the biometric signature with the ECG data; and
  transmitting the ECG data to the cardiologist workflow system only if the biometric signature is valid.

15. The method of claim 10, further comprising:
  receiving a biometric signature from the cardiologist, the biometric signature identifying the cardiologist;
  associating the biometric signature with the ECG data; and
  receiving the report from the cardiologist only if the biometric signature is valid.

16. The method of claim 10, wherein determining the cardiologist among the plurality of cardiologists to receive the ECG data and the measurement by the technician based on the requested review completion time and the amount of distributed ECG data and distributed measurements present in each cardiologist queue of a plurality of cardiologist queues by:
  determining a shift ending time for each cardiologist of the plurality of cardiologists; and
  identifying the cardiologist of the plurality of cardiologists having an ability to review the ECG data and the measurement before the requested review completion time and before the shift ending time for the cardiologist.

17. The method of claim 10, further comprising:
  determining an absence of ECG data for a patient at an end of an expected receipt time, the ECG data for the patient being expected to be received from at least one testing center; and
  transmitting a notification to the at least one testing center, the notification indicating that the ECG data for the patient is overdue.

18. The method of claim 10, further comprising:

receiving the report comprising a command to re-measure the ECG data; and transmitting the ECG data to the technician workflow system for re-measurement by a technician among the plurality of technicians in response to the command.

19. A system comprising:

a plurality of queues configured to store distributed electrocardiogram (ECG) data, wherein each queue of the plurality of queues is accessible to a technician or a cardiologist;

a device in communication with the each queue of the plurality of queues, the device comprising a processor configured to cause the device to:

receive patient information and ECG data originating from a testing center, the patient information and the ECG data being associated with a patient participating in a clinical trial conducted at the testing center and associated with a requested review completion time in accordance with the clinical trial;

receive an amount of distributed ECG data located in each queue of the plurality of queues;

for each queue of the plurality of queues, receive a shift ending time associated with the queue, the shift ending time corresponding to an end of a shift for the technician or the cardiologist capable of accessing the queue;

identifying the queue among the plurality of queues to which to distribute the ECG data based on:

the requested review completion time;

the amount of distributed ECG data located in each queue of the plurality of queues; and the shift ending time for each queue of the plurality of queues, to allow the technician or the cardiologist associated with the queue to complete an analysis of the ECG data before the requested review completion time, wherein the analysis comprises at least one of a measurement or a report; and distributing the ECG data to the queue among the plurality of queues identified to which to distribute the ECG data.

20. The system of claim 19, wherein the device is further capable of:

analyzing the ECG data originating from the testing center for one or more errors by comparing the ECG data to pre-set ECG parameters;

analyzing the patient information originating from the testing center for one or more errors by comparing the patient information to patient information parameters; and sending a notification to the testing center if the one or more errors for the ECG data or for the patient information is detected.

21. The system of claim 19, wherein the analysis is the report comprising the measurement, the device being configured to:

compare the measurement in the report to a predetermined parameter range;

redistribute the ECG data to a queue among the plurality of queues if the measurement is outside the predetermined parameter range; and transmit the report comprising the measurement to the testing center if the measurement is within the predetermined parameter range.

22. The system of claim 21, wherein the device is configured to:

receive a confirmation from at least one of the technician or the cardiologist that the measurement is outside the predetermined parameter; and transmitting the report comprising the measurement to the testing center.

23. The system of claim 21, wherein the analysis comprises a biometric signature from at least one of the technician or the cardiologist, the device being configured to:

determine a validity of the biometric signature; and transmit the report comprising the measurement to the testing center only if the biometric signature is valid.

24. The system of claim 19, wherein the device is further capable of:

determining an absence of ECG data for a patient at an end of an expected receipt time from the testing center; and transmitting a notification to the testing center, the notification indicating that the ECU data for the patient is overdue.

* * * * *

UNITED STATES PATENT AND TRADEMARK OFFICE
CERTIFICATE OF CORRECTION

| | |
|---|---|
| PATENT NO. | : 7,689,439 B2 |
| APPLICATION NO. | : 11/354062 |
| DATED | : March 30, 2010 |
| INVENTOR(S) | : Jason Parker |

It is certified that error appears in the above-identified patent and that said Letters Patent is hereby corrected as shown below:

In the Specification:

Column 10, Line 41. Please change "# 1" to --#1--

Column 11, Line 61. Please change "# 1's" to --#1's--

In the Claims:

Column 22, Line 42. Please change "ECU" to --ECG--

Signed and Sealed this

Eighth Day of June, 2010

David J. Kappos
*Director of the United States Patent and Trademark Office*